(12) United States Patent
Marchin

(10) Patent No.: US 11,725,094 B2
(45) Date of Patent: Aug. 15, 2023

(54) USE OF MATERIALS INCORPORATING MICROPARTICLES FOR AVOIDING THE PROLIFERATION OF CONTAMINANTS

(71) Applicant: PYLOTE, Dremil-Lafage (FR)

(72) Inventor: Loic Marchin, Mons (FR)

(73) Assignee: PYLOTE, Dremil-Lafage (FR)

( * ) Notice: Subject to any disclaimer, the term of this patent is extended or adjusted under 35 U.S.C. 154(b) by 169 days.

(21) Appl. No.: 15/319,144

(22) PCT Filed: Jun. 25, 2015

(86) PCT No.: PCT/FR2015/051730
§ 371 (c)(1),
(2) Date: Dec. 15, 2016

(87) PCT Pub. No.: WO2015/197992
PCT Pub. Date: Dec. 30, 2015

(65) Prior Publication Data
US 2017/0130027 A1 May 11, 2017

(30) Foreign Application Priority Data
Jun. 25, 2014 (FR) ...................... 1455871

(51) Int. Cl.
| | | |
|---|---|---|
| *G04B 9/00* | (2006.01) | |
| *H04N 13/204* | (2018.01) | |
| *A61L 2/238* | (2006.01) | |
| *C08K 3/22* | (2006.01) | |
| *C08K 3/015* | (2018.01) | |
| *A01N 59/16* | (2006.01) | |
| *A61L 2/00* | (2006.01) | |

(52) U.S. Cl.
CPC ............. *C08K 3/22* (2013.01); *A01N 59/16* (2013.01); *A61L 2/0082* (2013.01); *A61L 2/238* (2013.01); *C08K 3/015* (2018.01); *C08K 2003/2296* (2013.01)

(58) Field of Classification Search
CPC .................... C08K 2003/2296; C08K 3/22
See application file for complete search history.

(56) References Cited

U.S. PATENT DOCUMENTS

| | | |
|---|---|---|
| 5,047,488 A | 9/1991 | Tanaka et al. |
| 6,200,680 B1 * | 3/2001 | Takeda .................... A61K 8/27 423/111 |
| 7,169,402 B2 | 1/2007 | Gabbay |
| 2003/0091767 A1 | 5/2003 | Podhajny |
| 2005/0003728 A1 | 1/2005 | Foss |
| 2006/0083710 A1 * | 4/2006 | Joerger .................. A01N 43/16 424/76.1 |
| 2008/0047894 A1 | 2/2008 | Trogolo et al. |
| 2008/0286212 A1 | 11/2008 | Cooley |
| 2010/0166817 A1 | 7/2010 | Shen |
| 2011/0052662 A1 | 3/2011 | Nakano et al. |
| 2012/0088860 A1 | 4/2012 | Wissemborski et al. |
| 2017/0044021 A1 * | 2/2017 | Xing ....................... B01J 14/00 |

FOREIGN PATENT DOCUMENTS

| | | |
|---|---|---|
| CN | 1629226 A | 6/2005 |
| CN | 1942162 A | 4/2007 |
| CN | 101084163 A | 12/2007 |
| CN | 102448292 A | 5/2012 |
| EP | 0 360 962 | 4/1990 |
| FR | 3 020 766 A1 | 11/2015 |
| JP | H02-91009 | 3/1990 |
| JP | H03-247626 | 11/1991 |
| JP | H05-049682 | 3/1993 |
| JP | H10-230976 | 9/1998 |
| JP | 2002-370909 | 12/2002 |
| JP | 2003-125746 | 5/2003 |
| JP | 2003-231570 | 8/2003 |
| JP | 2006-213796 | 8/2006 |
| WO | 2006/050477 A2 | 5/2006 |
| WO | 2007/100172 | 9/2007 |
| WO | 2012/104844 A2 | 8/2012 |
| WO | 2014/193875 A1 | 12/2014 |
| WO | 2015/170060 A1 | 11/2015 |

OTHER PUBLICATIONS

International Search Report, dated Oct. 26, 2015, from corresponding PCT Application.

\* cited by examiner

*Primary Examiner* — Kyle A Purdy
(74) *Attorney, Agent, or Firm* — Nixon & Vanderhye

(57) ABSTRACT

A solid material including a matrix, dispersed in which are microparticles of at least one antimicrobial agent for preventing, limiting and/or eliminating the contamination of the material and/or the contamination of a composition which is in contact with the material for at least a given time, and/or preventing, eliminating and/or slowing down the formation of biofilms on the surface of the material, wherein the antimicrobial agent is an oxide of at least one positively charged metal ion and the antimicrobial agent does not migrate out of the material. Also, the use of such material for manufacturing an article, to the process for manufacturing the article, and to the article obtained. In particular, the article is selected from stoppers, lids, seals, caps, covers, plugs and valves intended for sealing bottles, flasks, jars, cans, canisters, barrels, tanks, or various containers used for packaging and/or storing food products, dietetic products, cosmetic products, dermatological products or pharmaceutical products.

11 Claims, 3 Drawing Sheets

USE OF MATERIALS INCORPORATING MICROPARTICLES FOR AVOIDING THE PROLIFERATION OF CONTAMINANTS

INTRODUCTION

The present application relates to the use of a solid material comprising a matrix in which microparticles are dispersed, where the said particles have an antimicrobial effect. The application also relates to the use of the said material for the manufacture of an article, the method of manufacture of the said article, and the article that is obtained.

TECHNICAL FIELD

Repeatedly used compositions, in particular, those for cosmetic or pharmaceutical products, are subject to contamination risks as a result of their exposure to: ambient air, and/or a means of application (an applicator, a finger, etc.), and/or the organ for which the composition is intended (for example, eye drops for an eye). Packaging, containers and/or delivery devices for such compositions may also be susceptible to contamination.

To prevent and/or slow down the contamination of compositions, the structure of the packaging, containers or delivery devices used for such compositions is generally designed to isolate the uncontaminated part of the composition from the part of the composition which is in contact with ambient air, a means of application, an organ, and/or any other potential source of contamination. Thus, the containers designed to contain compositions susceptible to be contaminated may include a physical means of sealing, such as closing caps, valves and/or membranes allowing the isolation of the two parts of the composition from each other. These containers require a specific and complicated manufacturing process, which increases the cost considerably. Moreover, even if such systems avoid the contamination of the part of the composition that has been isolated, they do not necessarily avoid the contamination of the part of the composition that is being delivered; for example, where a nozzle being used to deliver the composition is itself contaminated.

Alternatively, the incorporation of organic or nanoscale antimicrobial agents in the materials that make up all, or parts of the packaging, containers, or delivery devices has also been explored. Thus, in particular, plastic matrices comprising silver nanoparticles (nano-silver), zinc oxide nanoparticles or triclosan (5-chloro-2-(2,4-dichlorophenoxy)phenol), an organic biocide, have been used in packaging, containers or delivery devices for compositions susceptible to contamination. In particular, as a result of their size, these two types of agents (nano-objects and organic compounds) can migrate and diffuse to a significant extent from the matrix into the composition. Such migration is undesirable. On the one hand, this migration leads to "exhaustion" of the stock of antibacterial agent contained in the matrix, which means that a large amount of the agent must be incorporated to prevent the packaging, container, or dispenser device from losing its antibacterial properties. On the other, the potential or actual toxicity of organic antibacterial agents and nano-objects discourages the use of compositions that contain them, in particular, those to be used in the cosmetic and pharmaceutical sectors. Triclosan, in particular, has been identified as an endocrine disrupter in this respect. Zinc oxide nanoparticles, marketed as Zano® 20, by Umicore Zinc Chemicals are a typical example of the types of nanoparticles used for incorporation into plastic matrices.

For compositions susceptible to contamination, it would be beneficial to have the option of packaging, containers and/or delivery devices that can prevent and/or slow the contamination of the parts of compositions that are not in direct contact with sources of contamination (retro-contamination), the contamination of parts to be delivered, the contamination of the packaging, and the contamination of containers and/or delivery devices, and also prevent the migration of any antimicrobial agents incorporated into the packaging, containers and/or delivery devices through compositions. These packaging materials, containers and/or delivery devices should preferably be of simple mechanical design, preferably identical to that used for compositions not susceptible to contamination, whose manufacture can be carried out simply and inexpensively.

It is within this framework that the Applicant has demonstrated that the incorporation of specific microparticles into matrices, for example, polymeric matrices, allows antimicrobial properties to be imparted to the materials obtained, without the antimicrobial agents being able to migrate beyond the exterior of the material itself, in particular in applications where a composition is in contact with the material. These materials also allow the elimination and/or slowing of the formation of biofilms on the materials' surfaces. These materials can be used, in particular, in the manufacture of packaging containers and delivery devices for compositions susceptible to contamination.

SUMMARY OF THE INVENTION

A first object of the invention is the use of a solid material comprising a matrix and microparticles comprising or consisting of at least one antimicrobial agent to prevent, limit and/or eliminate contamination of the said material and/or the contamination of the composition that is in contact with this same material, for at least a given time, and/or prevent, suppress and/or slow down biofilm formation on the surface of the said material, wherein the antimicrobial agent does not migrate out of the material.

A second object of the invention is the use of a solid material comprising a matrix and microparticles comprising or consisting of at least one antimicrobial agent for the manufacture of an article susceptible to come into contact with at least one source of microbial contamination, wherein the antimicrobial agent does not migrate out of the material or the article.

A further object of the invention is an article made of a material comprising a solid matrix and microparticles comprising or consisting of at least one antimicrobial agent, wherein the article is susceptible to come into contact with at least one source of microbial contamination and wherein the antimicrobial agent does not migrate out of the material or the article.

A final object of the invention is a manufacturing process for an article susceptible to come into contact with at least one source of microbial contamination comprising a forming step of a solid material comprising a matrix and microparticles comprising or consisting of at least one antimicrobial agent, wherein the antimicrobial agent does not migrate out of the material or of the article.

DETAILED DESCRIPTION OF THE INVENTION

Figure 1:
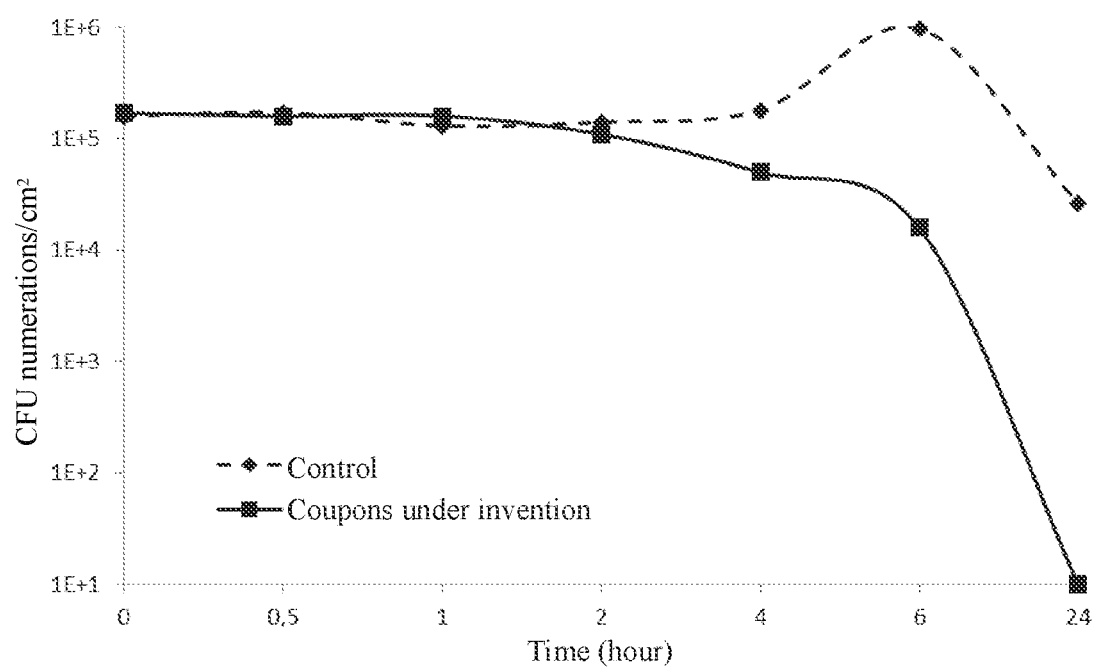
FIG. 1: Decrease in proliferation kinetics for a sample of material according to the invention and for a control sample (Example 1).

A first object of the invention is the use of a solid material comprising a matrix and a set of microparticles comprising or consisting of at least one antimicrobial agent to prevent, limit and/or eliminate contamination of the said material and/or the contamination of the composition that is in contact with the said material, for at least a given time, and/or prevent, suppress and/or slow down biofilm formation on the surface of the said material, wherein the antimicrobial agent does not migrate out of the material.

The microparticles within the set of microparticles incorporated into the material used according to the invention may be any type of microparticles comprising or consisting of at least one antimicrobial agent. The preferred choice is spherical microparticles. The preferred choice is for the entirety of the microparticles to be formed of a set of individualized microparticles, which are, preferably, uniformly distributed in the matrix, particularly at the surface level of the material, which might be in contact with the source of contamination.

The invention also has the object of a process to prevent, limit and/or eliminate contamination of a material and/or the contamination of the composition that is in contact with this same material, for at least a given time, and/or prevent, suppress and/or slow down biofilm formation on the surface of the said material, where the said process comprises the implementation or use of a solid material comprising a matrix and a set of microparticles, with the said microparticles comprising or consisting of at least one antimicrobial agent. In particular, the material does not allow the said antimicrobial agent to migrate to the exterior of the said material.

In the present invention, "antimicrobial agent" means a substance that kills, slows the growth of, or blocks the growth of, one or more microbes. In the present invention, "growth" means any cell operation that leads to a volumetric increase in a cell, the division of a cell, or cell reproduction. In the present invention, "microbe" means any unicellular or multicellular organism that is pathogenic or is parasitic to other organisms, such as humans. Microbes include moulds, fungi, yeasts, bacteria and viruses. An antimicrobial agent according to the present invention may be, for example, an agent that is antibiotic, fungicidal, fungistatic, bactericidal or bacteriostatic.

The terms fungicidal, fungistatic, bactericidal and bacteriostatic refer to agents that are, respectively, able to remove at least one type of mould, fungus or yeast, slow down the development of at least one type of mould, fungus or yeast, eliminate at least one type of bacteria, or slow down the development of at least one type of bacteria. The fungicide, fungistatic, bactericidal or bacteriostatic agent in the particles used according to the invention may be selected by a skilled person according to the conditions of use and the effect that is to be achieved.

The term bacterium refers to eubacteria and archaea. Eubacteria include firmicutes, gracilicutes and tenericutes. Gracilicutes include gram-negative bacteria such as Enterobacteriaceae, examples of which are *Klebsiella* (as *Klebsiella pneumoniae*) and *Escherichia* (as *Escherichia coli*). Fermicutes include gram-positive bacteria, such as Micrococcaceae, an example of which is *Staphylococcus* (such as *Staphylococcus aureus*), and stem-forming endospores including bacilli (Bacillaceae), for example, *Bacillus circulans*. All these references are mentioned in Bergey's Manual of Systematic Bacteriology, Williams & Wilkens, 1st ed. Vol. 1-4, (1984).

The term "moulds" here includes fungi and yeasts.

The term "fungus" means any fungus or fungi present in an environment. The term fungus (fungi) includes Amastigomycota, such as Deuteromycotina, which includes Deuteromycetes. The Deuteromycetes include *Aspergillus* (*Aspergillus niger*) and *Candida* (*Candida albicans*).

For this invention, the term biofilm refers to a community of multicellular microorganisms (for example, bacteria, fungi, algae or protozoa), which adhere to each other and to the surface of the material, and which are characterized by the secretion of an adhesive and protective matrix.

In one embodiment, the particles are the particles of an oxide (for example, a monoxide or a dioxide) of a positively charged metallic ion ($M^{n+}$ where n is an integer between 1 and 4), especially those with a double positive charge ($M^{2+}$), and where, more specifically, the metal oxide is not an oxide of copper. For example, zinc oxide, magnesium oxide, or titanium dioxide particles may be used, or a mixture or blend of such particles. In particular, it may be particles comprising a matrix of nanoparticles of such oxides that are used, in a matrix such as an amorphous silica matrix.

In a particular embodiment, there are particles containing zinc oxide (ZnO) or comprising or consisting of magnesium oxide (MgO), or comprising or consisting of a mixture of magnesium oxide and zinc oxide. In a more specific mode of carrying out the invention, the particles comprise or consist of zinc oxide (ZnO).

These particles, containing zinc or magnesium oxide, or a mixture of both, may also contain titanium dioxide. Titanium dioxide can be included up to a maximum proportion of 10% by weight, and preferably a maximum of 5% by weight, and, in particular, a maximum of 2% by weight, relative to the total weight of particles.

The particles, particularly metal oxide particles, used according to the invention can be doped with at least one chemical element known as a dopant. The dopant should preferably be suitable to increase and/or optimize the retarding properties of the metal oxide and/or the properties that suppress the proliferation of contaminants, preferably the fungicidal, fungistatic, bactericidal or bacteriostatic properties. For example, zinc oxide particles can be doped with at least one positively charged ion ($D^{m+}$, where m is an integer between 1 and 4), in particular, those of calcium, sodium, magnesium, titanium and/or aluminium.

The dopant is included up to a maximum concentration of 10% by weight, preferably a maximum of 5% by weight, and, in particular, a maximum of 2% by weight.

The particles can include, in addition to the substance with antimicrobial properties, another compound having particular properties. For example, the particles may include an active ingredient, such as an essential oil.

In one embodiment, the microparticles are mesoporous particles, optionally encapsulating a compound having particular properties, preferably antimicrobial, such as an essential oil. In one embodiment, the mesoporous microparticles are particles of an oxide of a metallic ion, as defined above, encapsulating a compound such as an essential oil.

The particles included in the material used according to the invention are microparticles, that is to say that their mean diameter (as a quantity) is between 0.1 and 1000 micrometres. In a particular mode of the invention, the particles have an average diameter of between 0.1 and 5 micrometres, preferably between 0.4 and 5 micrometres, especially between 0.5 and 3 or between 0.5 and 2 micrometres, in particular with an average diameter of about 0.5 micrometres. The skilled person knows the right techniques to be used to determine the value of the diameter of the particles, or aggregates of particles, according to the invention. For example, the average diameter of the particles in a set, standard deviation and size distribution can be determined, in particular, by statistical studies of microscopy images, for example, those generated by scanning electron microscopy (SEM) or transmission electron microscopy (TEM).

In this application, the term "about", where it is used in relation to a numerical value, means an interval centred on this same numerical value, and ranging from 10% above its value to 10% below its value.

In this invention, a set of individualized particles refers to a set of particles wherein the particles are not aggregated; that is to say that each particle in the set is not bound to any other particles by means of a strong chemical bond, such as a covalent bond.

A set of particles used according to the invention may optionally contain, on an ad hoc basis, particles that do not meet this criterion, provided the requirement for non-aggregation is complied with by at least 50%, by number, of the total number of particles. Preferably, at least 60%, at least 70%, at least 80%, at least 90%, and at least 95%, by number, of the particles of the set under consideration will be individualized.

Preferably, a particle used according to the invention is not composed of an aggregate of several smaller particles. This can be clearly analysed by visual means, for example, by scanning electron microscopy (SEM) or transmission electron microscopy (TEM). This means that the only possible constituents of the particles used according to the invention are crystallites of a size significantly less than that of the particles used according to the invention. A particle used according to the invention is preferably formed of at least two crystallites. A crystallite material is a type of material having the same structure as a single crystal; that is to say that within each atomic plane of its structure there are no major discontinuities of the crystalline order with the exception of point defects (vacancies or atoms inserted or substituted) or linear defects (dislocations).

Preferably, the particles used according to the invention are individualized and not deformable. Also, the surface of each particle which is in contact with other particles is generally very weak. In one embodiment, the radius of curvature of the meniscus forming the contact between two different particles of the set is less than 5%, preferably less than 2%, of the radius of each of the two particles, especially within a matrix used according to the invention.

The particles used according to the invention are spherical, in particular, they have a sphericity coefficient greater than or equal to 0.75. Preferably, the sphericity coefficient is greater than or equal to 0.8, greater than or equal to 0.85, greater than or equal to 0.9, or greater than or equal to 0.95.

The coefficient of sphericity of a particle is the ratio of the smallest diameter of the particle to its largest diameter. For a perfect sphere, the ratio is 1. The sphericity coefficient can be calculated, for example, by measuring the aspect ratio using any software adapted to deal with images, for example, images obtained by microscopy, in particular, scanning electron microscopy (SEM) or transmission electron microscopy (TEM).

A set of particles used according to the invention may optionally contain, on an ad hoc basis, particles that do not meet the criterion of having the required sphericity, to the extent that the average sphericity, as a quantity, of all the particles meets the criteria set-out as part of the present invention. Preferably at least 50%, at least 60%, at least 70%, at least 80%, at least 90%, and at least 95%, by number, of the particles of the set in question have a sphericity as defined above.

The micrometric particles, in particular, those according to the sizes defined above, have, more specifically, high specific areas. In a particular embodiment, the particles of the invention have specific areas greater than or equal to 15 $m^2/g$, preferably greater than or equal to 30 $m^2/g$. The specific surface area of the particles according to the invention can be up to 700 $m^2/g$ or 600 $m^2/g$. Naturally, the specific surface areas vary, particularly depending on the particle diameter and porosity. According to a particular mode of the invention, the mean diameter of the particles according to the invention is between 0.2 and 5 micrometres and preferably between 0.4 and 3 micrometres, and exhibiting specific surface areas greater than or equal to 15 $m^2/g$, preferably greater than or equal to 30 $m^2/g$. The specific surface areas can be measured by various methods, especially the Brunauer, Emmett, Teller (BET) method or the Barrett, Joyner, Halenda (BJH) method. The specific surface area values given above are measured according to the BET method unless otherwise specified.

In a particular embodiment, the particles are as described in the French patent application filed on 7 May 2014 as application number FR 14 54141 or PCT Patent Application No. PCT/ FR2015/ 051223 filed on 7 May 2015.

Individualized particles used according to the invention may be prepared by any method known to skilled workers in the field. In particular, they can be prepared by the method described in the French patent application filed on 7 May 2014 as application number FR 14 54141 or PCT Patent Application No. PCT/ FR2015/ 051223 filed on 7 May 2015.

This application describes a method of preparing a set of such particles known as "by aerosol pyrolysis" (or spray pyrolysis), which takes place at drying temperatures and not necessarily pyrolysis temperatures. In particular, this method comprises the following successive steps:

(1) the nebulization of a liquid solution containing a precursor to one or more inorganic material(s), from which the particles are to be formed, at a given molar concentration in a solvent, and which is used to obtain a spray of droplets of the solution, (2) the heating of the spray (referred to as drying) to a temperature sufficient to ensure the evaporation of the solvent and the formation of particles, (3) the heating of the particles to a temperature (referred to as pyrolysis) sufficient to ensure the decomposition of the precursor to form the inorganic material, (4) optionally, the densification of the particles, (4a) optionally, the quenching of the particles, and (5) the recovery of the particles thus formed.

More specifically, the method for preparing a set of particles according to the invention is usually carried out in a reactor. The set of particles thus obtained may correspond to large quantities, more specifically the amount obtained per day may be more than 100 g, 500 g, 1 kg, 15 kg or 20 kg, with this amount varying according to the feed rate of solution to the reactor that occurs/ is required. The set of particles created therefore has the advantage of being obtained in large quantities while maintaining the particle characteristics described above. Step (1) of the nebulization is performed preferably at a temperature of 10 to 40° C., and/or preferably for a duration less than or equal to 10 seconds, in particular, less than or equal to 5 seconds. In step (1), the liquid solution is generally in the form of an aqueous or hydroalcoholic solution or in the form of a colloidal sol. More specifically, the liquid solution in step (1) is introduced into a reactor by nebulization.

Step (2), the heating (drying) step, is preferably carried out at a temperature of 40 to 120° C., and/or preferably for a time period less than or equal to 10 seconds, in particular between 1 and 10 seconds.

Step (3), referred to as pyrolysis, is preferably carried out at a temperature of 120 to 400° C., and/or preferably for a time period less than or equal to 30 seconds, in particular between 10 and 30 seconds.

Step (4), the optional densification, may be performed over a wide range of temperatures, especially between 200 and 1000° C. This step is preferably carried out at a temperature of 400 to 1000° C., especially when the particles that are to be prepared are at least partly in crystalline form. When seeking to obtain dense but non-crystallized particles, especially amorphous particles, densification temperature can be lower, for example, it may be around 200° C. to 300° C., particularly for amorphous silica. Preferably, the densifying step is carried out for a duration less than or equal to 30 seconds, in particular between 20 and 30 seconds.

Step (5), particle recovery, is preferably carried out at a temperature below 100° C., and/or preferably for a period less than or equal to 10 seconds, in particular, less than or equal to 5 seconds. Step (5), particle recovery, is preferably carried out by deposition of the particles on a filter at the reactor outlet.

The temperature of each step may be outside the temperature ranges given above. For a given set of particles, the temperature to be applied can depend on the flow rate at which the drops and the particles circulate in the reactor. The more quickly the drops and the particles circulate in the reactor, the lower their residence time and higher the temperature required in the reactor to achieve the same result.

Preferably, steps (2), (3) and (4) are carried out in the same reactor. In particular, all the steps in the method (except the post-processing steps) are carried out in the same reactor.

The entirety of the steps in the method, especially steps (2), (3) and (4), are effected as a continuous sequence, one after the other. The temperature profile applied to the reactor is adapted as a function of the particles to be formed such that these three steps take place one after the other. Preferably, the temperature in the reactor is adjusted by means of at least one, and preferably three, heating elements, whose temperatures can be set independently.

Moreover, the method for preparing a set of particles according to the present invention preferably comprises a step (4a) in which the particles are quenched, which comes between step (3), or the optional step of particle densification (4), if there is to be one, and the particle recovery step (5). The quenching step (4a) corresponds to a rapid decrease in temperature. More specifically, if a particle densification step (4) is included, the quenching step is preferably carried out, and advantageously involves a temperature decrease of at least 300° C./s, in order to obtain, for example, a temperature between 15 and 50° C. More specifically, if a particle densification step (4) is not included, the quenching step may take place, and, if it takes place, it preferably corresponds to a temperature decrease of at least 100° C./s. The quenching step (4a) is preferably carried out by the input of a gas, preferably cold air, to all or part of the circumference of the reactor. In the present invention, a gas is considered cold if it is at a temperature between 15 and 50° C., preferably between 15 and 30° C. In one embodiment, the gas entering the reactor is a gas different from air. In particular, it may be a neutral gas (such as nitrogen or argon), a reducing gas (such as hydrogen or carbon monoxide), or any mixture of such gases.

The method for preparing a set of particles is carried out preferably in the absence of a flow of gas that transports the spray from the inlet (for example, at the bottom) of the reactor. The laminar flow to carry the material into the area with the highest temperature is best created by the suction end only (for example, the top) of the reactor, producing a depression, for example of the order of several pascals or tens of pascals.

Such an embodiment allows the use of a reactor without a gas inlet in its lower part, which limits process disturbances and losses, and maximizes the efficiency of the process and the size distribution of the particles obtained.

In another embodiment, the reactor in which the method is carried out also comprises an inflow of gas at the level where the spray is formed. The gas entering the reactor at this level is preferably air, in particular, hot air, that is to say at a temperature of 80 to 200° C.

Preferably, the method followed according to the invention does not include any further heating step in addition to those carried out within the aerosol pyrolysis reactor.

The precursor or precursors to the inorganic material(s) that is to be used to form the particles (in particular the metal oxides of positively charged ions, such as ZnO or MgO) may be of any origin. It (they) is (are) introduced in step (1) of the process as a liquid solution, especially an aqueous or hydroalcoholic solution containing the metal ions (in particular an organic or inorganic salt of the chosen metal) or as precursor molecules (such as organosilanes) or in the form of a colloidal sol (as a colloidal dispersion of nanoparticles of the metal or the oxide of the chosen metal). Preferably, the precursor or precursors to the inorganic materials is (are) introduced in step (1) of the process, as a liquid solution, especially an aqueous or hydroalcoholic solution containing the metal ions (such as an organic or inorganic salt of the chosen metal). The precursor(s) to the inorganic materials is (are) selected according to the type of particles to be formed.

The materials produced according to the invention have shown a high anti-contamination effectiveness despite the concentrations of particles incorporated into the matrix being low. Anti-contamination effectiveness can especially be measured according to the standard, ISO22196 (or JIS Z 2801), which allows an antibacterial action for plastic and other non-porous surfaces to be evaluated. Thus, in a particular aspect, the materials produced according to the invention were tested using this standard and found to have antibacterial activity between 0 and 7 $CFU/cm^2$, or between 1 and 7 $CFU/cm^2$, in particular between 2 and 7 $CFU/cm^2$, and more particularly between 4 and 5.3 $CFU/cm^2$. The skilled person will select the appropriate antimicrobial-activity criteria according to the application.

Low concentrations of particles are known to help prevent particle migration outside the material. The combination of anti-contamination effectiveness and the lack of particle release in the materials produced according to the invention may allow a reduction in the level of preservatives used, or even obviate the need for their use within compositions, especially in food and/or pharmaceutical, dermatological or cosmetic products that are in contact with these materials. To achieve the same rate of bacterial proliferation, it has been demonstrated that using materials produced according to the invention makes it possible, under some conditions, to make a fourfold reduction in the level of preservatives in a composition in contact with the plastic matrix. The combination of anti-contamination effectiveness and the lack of release of particles in materials developed according to the invention may even allow the composition's expiry date to be delayed. The material properties of the invention can also be used to reduce radiation doses, for example, gamma radiation, which are used for decontamination and/or sterilization of articles made with these materials. It is a well-known fact that sterilization by radiation has drawbacks. For example, it can contribute to discolouration and/or impart an odour to a package and/or cosmetic composition.

The matrix used to prepare the material according to the invention is advantageously a liquid matrix, whatever its viscosity, which allows the formation of a solid material that can be used according to the invention, following the incorporation of the entirety of the microparticles into the matrix, and, possibly following an additional optional step, such as a drying step. The characteristic "liquid" form of the matrix can be obtained by treating a non-liquid matrix; for example, by heating it. The incorporation of the microparticles into the matrix is preferably carried out when the matrix is in liquid or molten form; once the microparticles have been incorporated, the matrix is solidified in order to create a solid material.

Preferably, the matrix is an inorganic or organic matrix, for example, a polymeric matrix, especially a polymeric matrix of a plastic, rubber, varnish, paint, textile, silicone, glue, coating, or elastomer type. In a particular aspect, the polymeric matrix consists of thermoplastic polymers such as, in particular, acrylonitrile butadiene styrene copolymer, cellulose acetate, polystyrene, especially expanded polystyrene, polyamides, poly(butylene terephthalate), polycarbonates, high density polyethylene, low density polyethylene, poly(ethylene terephthalate), poly(methyl methacrylate), polyformaldehyde, polypropylene, poly(vinyl acetate), poly(vinyl chloride), poly(lactic acid) (PLA), polycaprolactone, polyhydroxyalkanoate (PHA), polysaccharides, styrene-acrylonitrile copolymer, or a mixture of such polymers.

In a particular mode of the invention, the polymer matrix is a matrix of a biopolymer; that is to say, a polymer derived from biomass, i.e. material produced by living organisms such as plants, algae, animals or fungi.

The matrix may also be a paint, an ink, or a matrix that is a precursor to a textile material or any material capable of forming films and/or coatings on surfaces. Textile materials include, in particular, clothing, carpets, curtains, bedding and medical textile materials such as bandages.

The proportion of microparticles distributed in the material may vary to a considerable extent depending on the nature of the particles and the matrix, and the intended use of the material and/or article. Preferably, the material or article of the invention comprises a low concentration of particles with respect to the matrix, in particular of 0.1 to 10%, or 0.1 to 5%, more specifically 0.5 to 3%, or 1 to 3% of the particles by weight relative to the total weight (the weight of the matrix and the particles). As a strong preference, the material or article used according to the invention contains about 0.2 to 2.5% by weight of particles relative to the total weight (the weight of the matrix and the particles).

A skilled person will be able to select the required proportion of particles in the material, in order to achieve the desired anti-contamination effect, especially the antimicrobial effect, and to maintain a release rate (in terms of particle migration outside of the material) that is as low as possible. The lower the concentration of particles in the material, the easier it becomes to maintain a low particle release rate. The materials used according to the invention have the characteristic of being able to maintain a very low (or zero) release rate, which corresponds to very low (or zero) particle migration levels, while, at the same time, the proportion of particles present is sufficient to achieve a significant antimicrobial effect.

The material used according to the invention thus has the property of suppressing and/or slowing down proliferation of contaminants. These properties are especially effective where the composition and/or the object susceptible to be contaminated is placed in close contact with the said material. In particular, the composition and/or the object susceptible to be contaminated is placed in contact with the material to slow and/or suppress the proliferation of contaminants.

In terms of effectiveness, the properties imparted to the material by the inclusion of particles in the matrix, according to the invention, remain undiminished, or only slightly diminished, over time, as a result of there being no transfer of the particles to the composition and/or the object. For example, the bactericidal action of zinc oxide particles is obtained by creation of reactive forms of oxygen, which, when the particles are in contact with oxygen in the air, kill the bacteria. There is no consumption of the zinc oxide particles, only the consumption of oxygen from the air or from the environment that the material is in.

In this invention, the fact that there is no migration of microparticles outside of the material, and, in particular, the fact that there is no transfer of the microparticles into the composition that is in contact with the material, means that there is less than 1 mg of the main element making up the microparticles, preferably less than 0.5 mg, and, in particular, less than 0.01 mg, to be found in each kilogram of the composition. The main constituent making up the microparticles is a metal oxide, as defined above, in particular, magnesium oxide and/or zinc oxide.

In particular, this concentration can be measured by the method that follows, as recommended by the European Pharmacopoeia (for example: chapters 3.1.3 for polyolefins, 3.1.5 for polyethylenes, or 3.1.6 for polypropylenes), where sample materials are first cut into pieces where the maximum length of any given side is 1 cm. 100 g of the material developed according to the invention and which is to be examined are introduced into a borosilicate glass conical flask with a ground neck. 20 mL of 0.1M hydrochloric acid are added. The mixture is heated under reflux for 1 hour with constant agitation. The solution is cooled to room temperature (i.e., between 18 and 25° C.) and allowed to settle. The extractables are measured by atomic absorption spectrometry. The tests enabled the measurement of a level of extractables of ≤1 ppm under these test conditions with a polypropylene matrix (the extractable being zinc, where the microparticles are based on ZnO).

Therefore, when the antimicrobial agent used according to the invention is a metal oxide in the form of microparticles, the phrase "the antimicrobial agent does not migrate out of the said material" can correspond to a metal-ion migration rate that is less than or equal to 50 ppm, to 25 ppm, in particular less than or equal to 10 ppm, or more specifically less than 5 ppm (the lower limit generally being between 0 and 1 ppm of the metal ion). The conditions under which these tests are carried out are more severe than the typical conditions encountered by the materials in normal use.

Of course, a migration rate outside of this range may be observed in very specific situations, especially when the material is placed in conditions that encourage degradation, for example, highly acidic conditions. However, such conditions are generally not found in food, cosmetic, dermatological or pharmaceutical applications.

Therefore, the materials used according to the invention retain the properties that enable them to suppress and/or slow the proliferation of contaminants for a longer time, compared with materials containing antimicrobial agents which may migrate out of the material. Preferably, the material retains these properties for a period that is longer than the period for which the composition in contact with the material is to be stored. In particular, the material retains these properties throughout its life.

Preferably, the composition that is in contact with the material used according to the invention is a food, dietary, cosmetic, dermatological or pharmaceutical composition. Preferably, it is a liquid, such as an ophthalmic solution, a cream, such as a cosmetic or dermatological cream, a gel, or a food product. Thus, according to a particular aspect of the invention, the composition is a physiologically acceptable composition to a mammal, particularly a human, that is to say, it does not cause abnormal reactions or functions to occur in the said mammal; no safety issues have been detected for this physiologically acceptable composition.

The time during which the composition is in contact with the material may vary to a considerable extent. Thus, when the material is used to manufacture a delivery device for a cosmetic lotion, the composition may remain in contact with the material for several weeks, months, or even years. When the material is used to make or coat ducts conveying food compositions, the composition may remain in contact with the material for much shorter times, of the order of a minute or a second, or even less than a second.

The use of a material developed according to the invention allows the composition that is contained in the article formed of the material developed according to the invention to be maintained in a clean state, that is to say, maintained free of any microbial contamination whose origin is its exposure, preferably its repeated exposure to ambient air and/or a means of application and/or the body for which the composition is intended.

The term "repeated exposure" means that the article is used at least twice to supply at least a portion of the composition, and, therefore, a part of the composition remains in contact with the article after the first use.

In addition, the orifice for delivering the composition, for example, the end of the outlet of a pump or tube, remains clean despite its contact with ambient air, the means of application and/or the body. Thus, there is no contamination of the part of the composition that will be delivered via this orifice during the next use, unlike systems presented previously, such as membrane systems or closing caps whose orifices can be contaminated.

In the case of food products, the use of a container developed according to the invention makes it possible to limit microbial growth especially on the surface of the food product, thereby delaying, or even eliminating the need for, a use-by-date whose determination usually takes into account the risk of bacterial growth.

Another object of the invention is the use of a material comprising a matrix and microparticles as defined above for the manufacturing of an article which may come into contact with at least one source of microbial contamination.

For this invention, the phrase "source of microbial contamination" means any part that may contain microbes and can transmit them to the material, the composition and/or article as they are defined in the present invention.

In one mode of carrying out the invention, the source of microbial contamination arises from either ambient air, the means of application, such as a brush or a spatula, or an organ of a human or animal body.

Another object of the invention is a manufacturing process for an article susceptible to come into contact with at least one source of microbial contamination, comprising a forming stage of a solid material, comprising a matrix and microparticles comprising or consisting of at least one antimicrobial agent, such as that described above.

The manufacturing process may include a preliminary step to disperse microparticles in the matrix. This dispersion can be achieved by simple mixing, or optionally, by use of mechanical or magnetic stirring, or sonication.

The manufacturing process thus comprises a forming step for the article, using any technique known to a skilled worker and designed to effect the forming of the matrix and/or material. Thus, for example, in the case of a polymeric matrix, the shaping step may be performed by injection moulding, injection stretch blow moulding, or extrusion blow moulding.

A further object of the invention is an article made of a solid material comprising a solid matrix and microparticles comprising or consisting of at least one antimicrobial agent, as previously defined, where the article may come into contact with at least one source of microbial contamination.

In one mode of carrying out the invention, the article forms all or part of the packaging, or a container or dispenser of a food, dietary, cosmetic, dermatological or pharmaceutical composition. The article developed according to the invention may be either single use or multi-use.

The article developed according to the invention is, in particular, likely to be selected from among the following: stoppers, seals, capsules, lids, plugs and taps for the closure of bottles, jars, pots, cans, barrels, tanks and various containers used for packaging and/or storage of food, dietetic, cosmetic, dermatological or pharmaceutical products.

Alternatively, the article may be all or a part of bottles, jars, pots, cans, barrels, tanks and various containers used for packaging and/or storage of food, dietetic, cosmetic, dermatological or pharmaceutical products.

In a preferred embodiment, the article is a container and/or a device for delivering a composition, particularly an ophthalmic solution, such as eye drops or the products for contact lenses. Advantageously, it is a single-use or multi-use bottle designed for pharmaceutical use. For example, a skilled person would be familiar with three-part ophthalmic product distribution devices. One, two, or all three of the three parts of the device can be produced with a material according to the invention.

Among the articles suitable for storage and/or distribution of pharmaceutical products, are spoons (such as spoons for syrup), syringes (such as syringes to administer, for example, a syrup), strips (such as strips of tablets or capsules), bags (such as infusion bags), tubes, cannulas, pumps and bottles.

Among the articles suitable for storage and/or distribution of food products, are trays, seals and packaging films.

Articles that may be in contact with sources of contamination include, in particular, piping, ductwork and work surfaces.

The various forms of packaging, containers or delivery devices of a food, dietary, cosmetic, dermatological or pharmaceutical composition are well-known in the art. For example, delivery devices used for a solution generally comprise a substantial cylindrical moulded body (including oval bodies) having a bottom, a mouth or cannula, and a resealable closure, especially a screw cap, on the upper part.

A material or an article according to the invention can be used in a wide variety of uses and fields. For example, such a material or article can be used to manufacture and/or coat the conduits carrying the components likely to be contaminated, in particular, on an industrial site. For example, the material, or the article, can be used to make the ducts that transport the food, or food products, in a food processing plant. The use of a material or an article according to the invention then makes it possible to limit the formation of biofilms and the development and/or proliferation of germs. This allows the avoidance, or a reduction in the frequency, of washing ducts, which often involves specific techniques and requires isolation of the ducts for a considerable time, something that can affect the productivity of the plant. In addition, the use of articles or materials produced according to the invention allows the desired effect to be obtained over the entire surface, even in hidden areas or, for example, areas to which access for the purpose of cleaning is difficult.

Similarly, articles and/or materials produced according to the invention can be used to manufacture equipment for any environment susceptible to contamination, such as operating theatres, sterile rooms, surgical instrument environments or laboratory benches.

The following examples are included for illustrative purposes only and do not limit the present invention.

EXAMPLES

Example 1

Evaluation of the Antibacterial Effect of Materials Produced According to the Invention The proliferation of different types of bacteria (*Escherichia coli*, *Staphylococcus aureus*, *Pseudomonas aeruginosa*, *Listeria monocytogenes*, *Salmonella enterica*, *Staphylococcus epidermidis*, *Streptococcus pneumoniae* and *Haemophilus influenzae*) was studied in samples of material produced according to the invention and compared with that observed for equivalent samples containing no particles. The tests were conducted according to the standard, JIS Z 2801: 2010. The tests were performed in triplicate and the results shown below correspond to the mean results for the three samples.

The bacterial strains *Listeria monocytogenes* and *Salmonella enterica* are typically associated with the development of bacterial contamination in food products.

The bacterial strains *Staphylococcus epidermidis*, *Streptococcus pneumoniae* and *Haemophilus influenzae* are typically associated with the development of bacteria in the nasal area, and are therefore likely to be present on any item that comes into contact with the face.

The sample of material produced according to the invention is a piece of low density polyethylene (Purell PE 1840 H sold by the Lyondelbasell company) comprising spherical particles of zinc oxide of average diameter 0.50 μm, with a specific surface area of about 15 m²/g, synthesized by the method described in patent application number FR 14 54141. The concentration of spherical particles of zinc oxide is 2% by weight.

The control sample is also a piece of low density polyethylene plate (Purell PE 1840 H sold by the Lyondelbasell company).

The bacterial reference strains are the following: *Escherichia coli* CIP 53126 and *Staphylococcus aureus* CIP 53156.

The sample pieces were treated with alcohol. The set of sample pieces was then rinsed with sterile distilled water and dried under a laminar flow hood, prior to the tests being carried out. The covering film is a sterile film made of Stomacher bags (40 mm×40 mm) (AES).

The suspensions were prepared with Nutrient Broth solution diluted to a concentration of 1/500. The recovery solution is SCDLP solution as recommended by the standard. Subsequent dilutions are carried out using PBS (phosphate buffered saline). The medium is Trypticase soy agar (Biomerieux).

Depositions of amount 1.83×105 CFU (Colony Forming Units) were made on the sample pieces. Proliferation is measured 24 hours after deposition, or one hour after the deposition (for *Streptococcus pneumoniae* and *Haemophilus influenzae*).

The results are shown in Table 1 below, the contamination value having been normalized to 1 for the control sample (without particles).

TABLE 1

| Strain | Proliferation for the sample of material produced according to the invention | Proliferation for the control sample |
|---|---|---|
| *Escherichia coli* | 0.000628765 | 1 |
| *Staphylococcus aureus* | 0.009632989 | 1 |
| *Pseudomonas aeruginosa* | 0.459916667 | 1 |
| *Listeria monocytogenes* | $6.21 \times 10^{-5}$ | 1 |
| *Salmonella enterica* | $1.43 \times 10^{-6}$ | 1 |
| *Staphylococcus epidermidis* | 0.011402338 | 1 |
| *Streptococcus pneumoniae* | 0.41005694 | 1 |
| *Haemophilus influenzae* | 0.300787534 | 1 |

Proliferation on the samples of material produced according to the invention is significantly lower than for samples containing no particles, for all types of bacteria tested.

The proliferation of bacteria was followed over a 24-hour test period for *Escherichia coli*. FIG. 1 shows the kinetics of the decrease in proliferation for the samples of material produced according to the invention and for the control sample.

Other low density polyethylene samples (of Purell PE 1840 H sold by the Lyondelbasell company) comprising spherical particles as specified above can be prepared, with particle concentrations ranging from 0.2 to 2.5% by weight.

Example 2

Study of the Influence of the Material Produced According to the Invention on the Quantity of Preservatives Required A quantity of the nutrient solution (Nutrient Broth) is deposited on a sample of material produced according to the invention and on a control sample as defined in Example 1. The dose of preservative (methylparaben) in the Nutrient Broth solution was varied, and the subsequent rate of proliferation of *Escherichia coli* was compared under various conditions after 6 hours and after 24 hours of testing. The concentrations of preservative in solution are expressed as percentages by weight.

Figure 2:
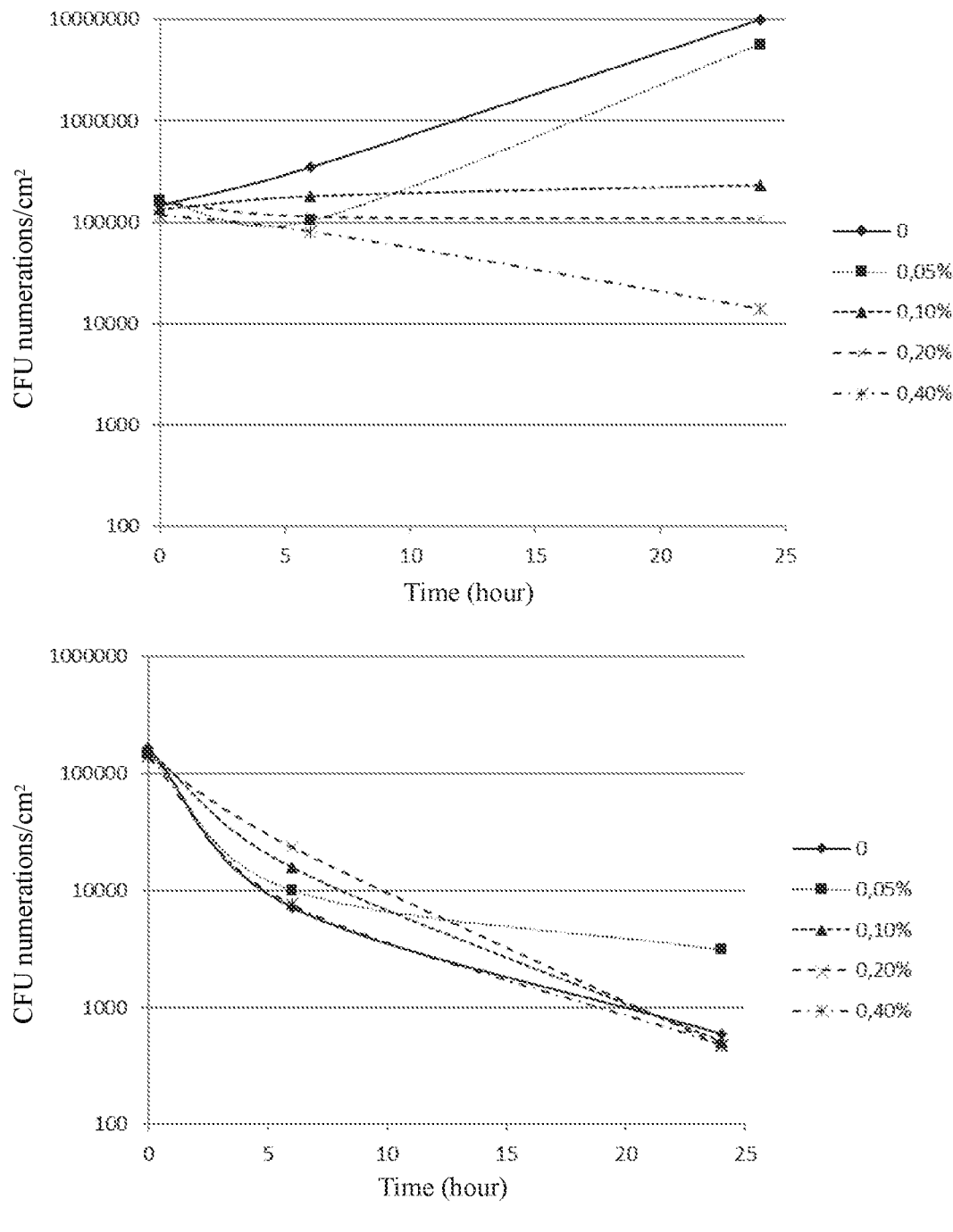
FIG. 2: Evolution of bacterial growth as a function of preservative concentration for a control sample (a) and for a sample of material according to the invention (b) (Example 2).

FIG. 2 shows the evolution of the growth of bacteria based on concentrations of preservative for the control sample (a) and for the sample of material produced according to the invention (b).

Figure 3:
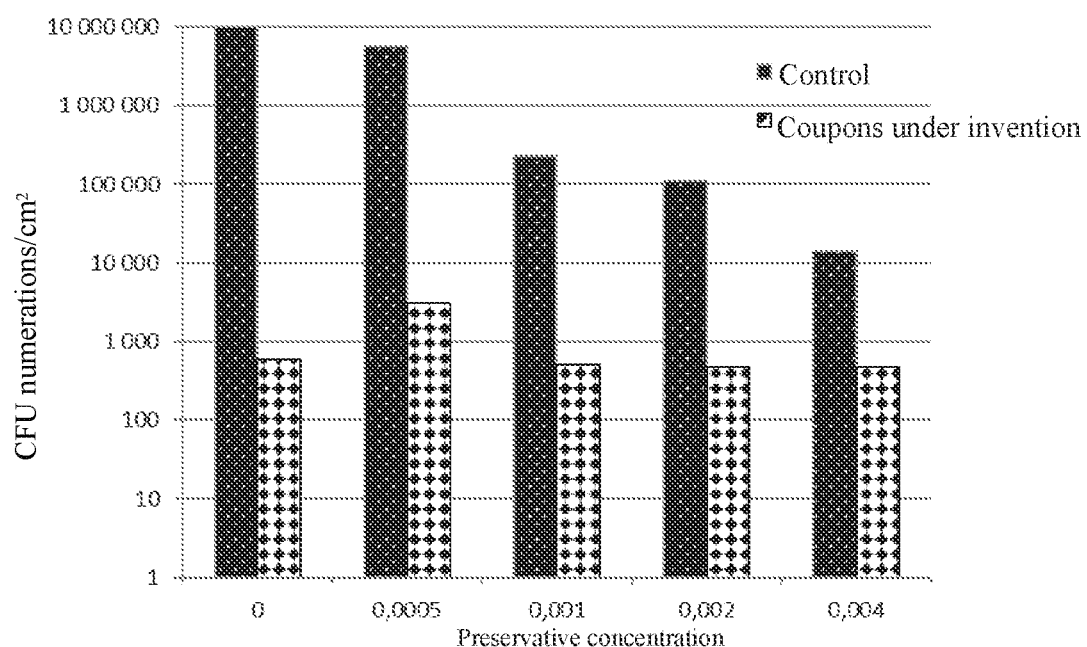
FIG. 3: Comparison of the antibacterial action of a control sample and a material sample according to the invention, depending on the concentration of preservative (Example 2).

FIG. 3 shows a comparison of antibacterial action, as a function of preservative concentration, for the control sample and the sample of material produced according to the invention.

Equivalent antibacterial activity is obtained for sample material produced according to the invention with 0.1% preservative solution, and for the control sample with 0.4% preservative solution.

Therefore, compared with a composition in contact with a material containing no particles, use of the material produced according to the invention, when it is in contact with the same composition, can reduce the amount of preservative required by a factor of four.

Example 3

Retro-Contamination Study

This example relates to the evaluation of the treatment capacity of a bottle of a product, such as eye drops, after simulated use for 14 days and the regular application of potential contaminants of human origin (*Staphylococcus aureus*, *Pseudomonas aeruginosa* and *Bacillus subtilis*).

Materials and Methods

The following strains are used: *Staphylococcus aureus* CIP 4.83, *Pseudomonas aeruginosa* CIP 82118 and *Bacillus subtilis* (in spore form) CIP 52.62. Conservation and maintenance of the strains are carried out according to standard EN 12353 (September 2006). The stock bacterial suspensions are made in accordance with the European Pharmacopoeia (7th edition, 2012, Chap. 2.6.12). Working suspensions are created from the stock solution by preparing six successive decimal dilutions in a sterile suspension liquid containing 9 g/l of tryptone-salt (corresponding to a theoretical adjustment from $1.10^2$ to $3.10^2$ CFU/ml). The suspensions are counted using a plating method.

The control vial comprises the vial, end-piece and a polyethylene cap (Purell 1840H). The test vial comprises a vial, an end-piece, and a cap, of material made according to the invention (polyethylene of type Purell 1840H containing spherical particles of ZnO of average diameter 500 nm and a specific surface area of about 15 m²/g). The vial, the end-piece and the cap contain 2% by weight of spherical particles of ZnO.

The two vials are filled with 9 ml of 1/500 Nutrient Broth solution (containing 3 g meat extract, 10 g soy peptone, 5 g NaCl: quantity sufficient for 1l). The pH is between 6.8 and 7.2. The protocol was applied to ten test vials and ten control vials.

For two weeks, eight simulations are performed at a rate of four simulations a week on both types of vials. The simulation procedure is repeated twice in a day.

The method of operation of the simulation procedure is:
Preparation of the working suspensions of the three microorganisms as described above,
Preparation of an extemporaneous mixture of 10 ml containing the three suspensions of equal volumes
Liberally soak a sterile swab with this suspension,
Unscrew the cap and remove a drop of product in the normal way,
Simulate use by applying the soaked swab to the product distribution area, and
Screw the cap back on and store the vials at room temperature until the next simulation.

The concentration of microorganisms present in the broth is assessed after 7 days, and again after 14 days. After 14 days, the sterility of the broth is also checked in the control vial.

In terms of the count, the assay was performed according to the recommendations in Chapter 2.6.12 of the European Pharmacopoeia. After homogenization of the contents of the vial by vortexing, 2×100 μL volumes were added to a medium of Trypticase soy agar (Biomerieux) providing all the aerobic flora and Sabouraud (AES) providing all the fungal flora. The plates were incubated at 32.5±2.5° C. for 3 to 5 days for the Trypticase soy medium, and 22.5±2.5° C. for 5 to 7 days for the Sabouraud medium.

Sterility evaluation tests were carried out according to the recommendations of Chapter 2.6.1 of the European Pharmacopoeia. It was carried out only on the vials of material made according to the invention and according to two modes of sampling.

For the vials numbered 1 to 5, the broth was collected after passage through the end-piece, in order to test it under the most unfavourable conditions.

For the vials numbered 6 to 10, the broth was collected directly from the inside of the vial, after unscrewing and taking off the end-piece.

The whole broth (about 8.5 ml) contained in different vials was sampled then introduced into 100 ml of (Biomerieux) Trypticase soy broth. Incubation was carried out at 22.5±2.5° C. for 14 days. The observation of contamination indicates a positive test. In this case only, isolation was carried out to allow identification of the contamination.

Two types of control were produced:
Negative Control:
A polyethylene vial containing 9 ml of broth was placed in the same environmental conditions as the vials used in the test in order to validate the degree of sterility after 14 days of simulation.
Positive Control:
A polyethylene vial containing 9 ml of broth was inoculated with the three bacteria (to a final concentration of about 3 CFU/ml) and placed under the same ambient conditions as used in the tests in order to confirm that the viability of microorganisms is maintained during the 14 days of simulation.

Results

The results presented in the tables below are expressed in units of CFU per 100 microlitres of broth.

Enumeration

Table 2 below shows the results of enumeration at 7 and 14 days on the Trypticase soy agar medium. The vials of material produced according to the invention are the "PE+ZnO" vials; the other vials ("PE" vials) are the polyethylene control vials.

TABLE 2

| Sample | 7 days | | 14 days | |
| --- | --- | --- | --- | --- |
| | PE vial | PE + ZnO vial | PE vial | PE + ZnO vial |
| No. 1 | 33** | <1 | >300** | <1 |
| No. 3 | 2** | <1 | >300** | <1 |
| No. 4 | 6* | <1 | >300** | <1 |
| No. 5 | 1** | <1 | >300** | 2** |
| No. 6 | >300* | <1 | >300** | <1 |

TABLE 2-continued

|  | 7 days | | 14 days | |
| --- | --- | --- | --- | --- |
| Sample | PE vial | PE + ZnO vial | PE vial | PE + ZnO vial |
| No. 7 | 1** | <1 | >300** | <1 |
| No. 8 | 1** | <1 | >300** | <1 |
| No. 9 | >300** | <1 | >300** | <1 |
| No. 10 | >300 | <1 | >300 | <1 |
| Negative control | <1 | <1 | <1 CPU | <1 |
| Positive control | >300* | >300* | >300* | >300* |

*Detection of Pseudomonas aeruginosa and Bacillus subtilis
**Majority detection of Pseudomonas aeruginosa Table 3 below shows the count results at 7 and 14 days on the Sabouraud medium. The vials of material produced according to the invention are the "PE+ZnO" vials; the other vials ("PE" vials) are the polyethylene control vials.

TABLE 3

|  | T7 days | | T14 days | |
| --- | --- | --- | --- | --- |
| Sample | PE vial | PE + ZnO vial | PE vial | PE + ZnO vial |
| No. 1 | 28 | <1 | >300 | <1 |
| No. 2 | 5 | <1 | >300 | <1 |
| No. 3 | 2 | <1 | >300 | <1 |
| No. 4 | 13 | <1 | >300 | <1 |
| No. 5 | 1 | <1 | >300 | 1 |
| No. 6 | >300 | <1 | >300 | <1 |
| No. 7 | 1 | <1 | >300 | <1 |
| No. 8 | <1 | <1 | >300 | <1 |
| No. 9 | >300 | <1 | >300 | <1 |
| No. 10 | >300 | <1 | >300 | <1 |
| Negative control | <1 | <1 | <1 | <1 |
| Positive control | >300 | >300 | >300 | >300 |

The population observed on the Sabouraud agar is mainly bacterial in origin (mainly *Pseudomonas aeruginosa*) except for polyethylene vial No. 6, where the presence of moulds was detected in addition to the bacterial flora majority.

After 7 days of simulation, no vial of the 10 tested in the PE+ZnO series (vials of material produced according to the invention) showed the presence of contamination. At the same time, nine vials of the ten tested in the PE series (the control vials) were contaminated, the contamination level being heterogeneous from 1 CFU to 300 CFU detected.

After 14 days of simulation, a single vial of the ten tested in the PE+ZnO series (vials of material produced according to the invention) showed the presence of *Pseudomonas aeruginosa*. At the same time, all vials in the PE series (the control vials) were contaminated, showing a high degree of contamination of greater than 300 CFU per 100 µl of broth.

Evaluation of Sterility

Table 4 below summarizes the control sample sterility test results for the vials produced according to the invention for which samples were taken directly from inside the vial.

TABLE 4

| Sample | Growth | Identification |
| --- | --- | --- |
| No. 6 | Negative | — |
| No. 7 | Negative | — |
| No. 8 | Negative | — |
| No. 9 | Negative | — |
| No. 10 | Negative | — |
| Negative control | Negative | — |
| Positive control | Positive | Pseudomonas aeruginosa Staphylococcus aureus |

The results demonstrate maintenance of sterile conditions in the broth for the five vials where the samples were collected directly from inside the container.

Conclusion

The use of a material produced according to the invention, for the vial and the end-piece, allows the risk of contamination of the broth under the test conditions to be limited, namely artificial contamination of the end-piece, associated with a gram-positive bacterium (*S. aureus*), a gram-negative bacterium (*P. aeruginosa*), and a gram negative bacterium in spore form (*Bacillus subtilis*).

Under the same conditions, the use of polyethylene control vials is characterized by retro-contamination with significant growth of at least one of the three contaminants.

Sterility controls carried out on the vials of material produced according to the invention confirm the absence of retro-contamination of the product contained in the package.

Example 4

Antimicrobial Activity Study

All the materials in the examples above (both inorganic and organic materials, such as plastic, rubber, varnish, paint, textile, silicone, glue, coatings, and elastomers) have been tested according to the standard, ISO22196, and the results correspond to an antibacterial activity in *Escherichia coli* samples of between 1 and 7 CFU/cm$^2$. The concentrations of particles by weight (with total weight comprising the matrix and the particles) are 0.2 to 2%, and the specific surface areas of the particles are 15 to 30 m$^2$/g for an average particle diameter of 0.50 µm.

The test described by the standard requires the use of three treated samples (40 mm×40 mm) and six untreated samples for each microorganism to be analysed.
  A. Inoculation with a known concentration of the microorganism to be tested, deposited homogeneously on the sample surface,
  B. Determination of the concentration of viable microorganisms, performed immediately after inoculation, and after 24 hours of incubation of the culture, using the method based on the agar medium,
  C. The comparison of these counts allows determination of the value of the antimicrobial activity on the surface analysed.

The test equipment is treated with alcohol. All test equipment is rinsed with sterile distilled water and then dried under a laminar flow hood prior to testing.

The sterile film is made from Stomacher bags (40 mm×40 mm).

Test conditions:
Contact temperature: 36±1° C.
Relative Humidity: 80%
Contact time: 24 hours
Results
For MgO particles:
  MgO with a polyethylene matrix of low density RIBLENE (tests according to ISO22196 *E. coli*)

T0 control 1.38×10$^5$ CFU
T0 sample: 1.44×10$^5$ CFU
T24h control: 2.83×10$^7$ CFU
T24h sample: 60 CFU For particles of ZnO and MgO (quantities: 0.5% and 0.2% respectively by weight):

ZnO/MgO (weight ratio 2.5) with a low density polyethylene matrix of Purell PE 1840 H (tests carried out according to ISO22196 *E. coli*)

T0 control 1.67×10$^5$ CFU
T0 sample: 1.72×10$^5$ CFU
T24h control 2.56×10$^7$ CFU
T24h sample: 196 CFU

The invention claimed is:

1. A method for preventing and/or eliminating contamination of a solid material, and/or contamination of a composition that is in contact with said solid material, for at least a given time, and/or for preventing and/or suppressing biofilm formation on a surface of the said solid material, wherein said contamination is a contamination by *Staphylococcus aureus* and/or said biofilm formation is a biofilm formation by *Staphylococcus aureus*, comprising forming a solid material comprising a matrix and a set of individualized microparticles uniformly distributed within the matrix comprising or consisting of at least one antimicrobial agent, wherein the antimicrobial agent is an oxide of at least one positively charged metal ion and where the antimicrobial agent does not migrate out of the solid material, and wherein:

at least 80% of the microparticles in the set have a sphericity coefficient of 0.85 or more, and at least 90% of the microparticles in the set have a sphericity coefficient of 0.75 or more, at least 90% of the microparticles in the set are non-aggregated, the concentration of said microparticles is 0.1 to 10%, by weight, based on the weight of the matrix and particles, said microparticles have specific areas greater than or equal to 15 m$^2$/g, as measured according to the BET method, and the individualized microparticles uniformly distributed within the matrix are non-aggregated within the matrix and have a mean diameter between 0.5 and 5 micrometers, as measured by microscopy of the matrix.

2. The method according to claim 1, wherein the concentration of the microparticles is 0.1 to 5%, by weight, based on the weight of the matrix and particles.

3. The method according to claim 1, wherein the microparticles comprise zinc oxide or are constituted of zinc oxide (ZnO), or comprise magnesium oxide or are constituted of magnesium oxide (MgO), or a mixture of magnesium oxide and zinc oxide.

4. The method according to claim 3, wherein the microparticles are selected from ZnO microparticles, microparticles of ZnO doped with sodium or aluminium, and mesostructured microparticles comprising ZnO.

5. The method according to claim 1, wherein the matrix is a polymeric matrix.

6. The method according to claim 5, wherein the polymer matrix is a thermoplastic matrix polymer selected from acrylonitrile butadiene styrene copolymer, cellulose acetate, polystyrene, polyamides, poly(butylene terephthalate), the polycarbonates, polyethylene, poly(ethylene terephthalate), poly(methyl methacrylate), polyformaldehyde, polypropylene, poly(vinyl acetate), poly(vinyl chloride), poly(lactic acid) (PLA), p olycaprolactone, polyhydroxyalkanoate (PHA), polysaccharides and the copolymer styrene-acrylonitrile.

7. The method according to claim 1, wherein the composition is physiologically acceptable to a mammal and is preferably selected from a food composition, a dietary composition, a cosmetic composition, a dermatological composition or a pharmaceutical composition.

8. A method for preventing and/or eliminating contamination of a solid material, and/or contamination of a composition that is in contact with said solid material, for at least a given time, and/or for preventing and/or suppressing biofilm formation on a surface of the said solid material, wherein said contamination is a contamination by *Staphylococcus aureus* and/or said biofilm formation is a biofilm formation by *Staphylococcus aureus*, said method, comprising:

(i) preparing a set of microparticles by a process comprising:
   (1) the nebulization, at a temperature ranging from 10° C. to 40° C., of a liquid solution containing a precursor to one or more inorganic material(s), from which the particles are to be formed, at a given molar concentration in a solvent, and which is used to obtain a spray of droplets of the solution,
   (2) the heating of the spray to a temperature ranging from 40° C. to 120° C., to ensure the evaporation of the solvent and the formation of particles,
   (3) the heating of the particles to a temperature ranging from 120° C. to 400° C., to ensure the decomposition of the precursor to form the inorganic material,
   (4) optionally, the densification of the particles,
   (4a) the quenching of the particles, and
   (5) the recovery of the particles thus formed; and (ii) forming a solid material comprising a matrix and said set of individualized microparticles uniformly distributed within the matrix;

wherein:
said microparticles comprise or consist of at least one antimicrobial agent, wherein the antimicrobial agent is an oxide of at least one positively charged metal ion, said antimicrobial agent does not migrate out of the solid material, at least 80% of the microparticles in the set have a sphericity coefficient of 0.85 or more, and at least 90% of the microparticles in the set have a sphericity coefficient of 0.75 or more, at least 90% of the microparticles in the set are non-aggregated, the concentration of said microparticles is 0.1 to 10%, by weight, based on the weight of the matrix and particles, said microparticles have specific areas greater than or equal to 15 m$^2$/g, as measured according to the BET method, and the individualized microparticles uniformly distributed within the matrix are non-aggregated within the matrix and have a mean diameter between 0.5 and 5 micrometers, as measured by microscopy of the matrix.

9. The method according to claim 1, wherein the concentration of the microparticles is 0.2 to 2%, by weight, based on the weight of the matrix and particles.

10. The method according to claim 1, wherein the concentration of the microparticles is 0.2 to 0.5%, by weight, based on the weight of the matrix and particles.

11. The method according to claim 8, wherein the quenching is carried out at a temperature decrease of at least 100° C./s to obtain a temperature between 15 and 50° C.

* * * * *